United States Patent
Horvath et al.

(10) Patent No.: US 9,115,077 B2
(45) Date of Patent: Aug. 25, 2015

(54) PROCESSES AND INTERMEDIATES FOR PREPARING A MACROCYCLIC PROTEASE INHIBITOR OF HCV

(71) Applicant: Janssen Pharmaceutica NV, Beerse (BE)

(72) Inventors: Andras Horvath, Turnhout (BE); Dominic John Ormerod, Hoogstraten (BE); Dominique Paul Michel Depre, Hamme-Mille (BE); Veronique Cerpentier, Loksbergen (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/552,550

(22) Filed: Nov. 25, 2014

(65) Prior Publication Data
US 2015/0080577 A1    Mar. 19, 2015

Related U.S. Application Data

(63) Continuation of application No. 13/141,715, filed as application No. PCT/EP2009/067715 on Dec. 22, 2009, now Pat. No. 8,927,722.

(30) Foreign Application Priority Data

Dec. 23, 2008   (EP) .................................... 08172691

(51) Int. Cl.
C07D 215/00 (2006.01)
C07D 231/12 (2006.01)
C07C 67/475 (2006.01)
C07C 231/12 (2006.01)
C07C 235/40 (2006.01)
C07D 307/33 (2006.01)
C07D 417/04 (2006.01)
C07D 453/04 (2006.01)

(52) U.S. Cl.
CPC ............. *C07C 67/475* (2013.01); *C07C 231/12* (2013.01); *C07C 235/40* (2013.01); *C07D 307/33* (2013.01); *C07D 417/04* (2013.01); *C07D 453/04* (2013.01); *C07C 2101/08* (2013.01)

(58) Field of Classification Search
CPC ............................ C07D 215/00; C07D 231/12
USPC ......................................................... 435/152
See application file for complete search history.

(56) References Cited

U.S. PATENT DOCUMENTS 6,365,755 B1    4/2002  Sumi et al.
8,212,043 B2 *  7/2012  Horvath et al. ............... 546/157

FOREIGN PATENT DOCUMENTS

| CN | 101146794 A | 3/2002 |
|---|---|---|
| EP | 0118934 A1 | 9/1984 |
| JP | S59148749 A | 8/1984 |
| JP | S6124539 A | 2/1986 |
| JP | H11199542 A | 7/1999 |
| JP | 2002-069069 A | 12/2009 |
| JP | 2011-541509 A | 12/2009 |
| WO | WO 2005/073195 A2 | 8/2005 |
| WO | WO 2005/073216 A2 | 8/2005 |
| WO | WO 2007/014921 A1 | 2/2007 |
| WO | WO 2007/014926 A2 | 2/2007 |
| WO | WO 2008/092955 A | 8/2008 |
| WO | WO 2010/072742 A1 | 7/2010 |

OTHER PUBLICATIONS

Raboisson et al., "Structure-Activity Relationship Study on a Novel Series of Cyclopentane-Containing Macrocyclic Inhibitors of the Hepatitis C Virus NS3/4A Protease to the Discovery of TMC435350", Bioorganic & Medicinal Chemistry Letters, vol. 18, pp. 4853-4858 (2008).

Zhao-Hiu Zhou et al., Xiamen University Journals (Natural Science), vol. 38, No. S1.

Honda, "A Synthesis of (+)-Brefeldin A", Tetrahedron Letters, vol. 22, No. 28, pp. 2679-2682 (1981).

Rosenquist, "Synthesis of Enantiomerically Pure trans-3,4-Substituted Cyclopentanois by Enzymatic Resolution", Acta Chemica Scandinavica, vol. 46, pp. 1127-1129 (1992).

* cited by examiner

*Primary Examiner* — Niloofar Rahmani
(74) *Attorney, Agent, or Firm* — Andrea Jo Kamage

(57) ABSTRACT

The present invention relates to the cinchonidine salt (XXa)

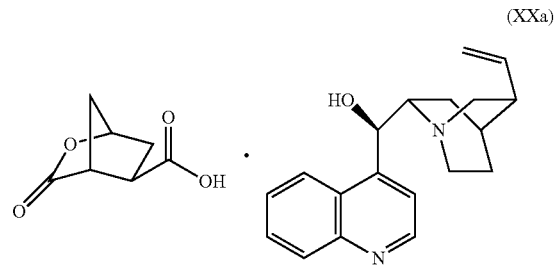

useful in the preparation of intermediates for preparing a macrocyclic HCV inhibitor, as well as processes involving this salt.

1 Claim, No Drawings

PROCESSES AND INTERMEDIATES FOR PREPARING A MACROCYCLIC PROTEASE INHIBITOR OF HCV

CROSS REFERENCE TO RELATED APPLICATIONS

This application is a continuation of prior application Ser. No. 13/141,715 filed, Jun. 23, 2011, currently allowed, which claims priority of the benefits of the filing of PCT Application No. PCT/EP2009/067715, filed Dec. 22, 2009, and European Patent Application No. EP08172691.1 filed Dec. 23, 2008. The complete disclosures of the aforementioned related applications are hereby incorporated by reference for all purposes.

FIELD OF THE INVENTION

The present invention relates to synthesis procedures and synthesis intermediates of a macrocyclic protease inhibitor of the hepatitis C virus (HCV).

BACKGROUND OF THE INVENTION

Hepatitis C virus (HCV) is the leading cause of chronic hepatitis, which can progress to liver fibrosis leading to cirrhosis, end-stage liver disease, and HCC (hepatocellular carcinoma), making it the leading cause of liver transplantations. Current anti-HCV therapy, based on (pegylated) interferon-alpha (IFN-α) in combination with ribavirin, suffers from limited efficacy, significant side effects, and is poorly tolerated in many patients. This prompted the search for more effective, convenient and better-tolerated therapy.

Replication of the genome of HCV is mediated by a number of enzymes, amongst which is HCV NS3 serine protease and its associated cofactor, NS4A. Various agents that inhibit this enzyme have been described. WO 05/073195 discloses linear and macrocyclic NS3 serine protease inhibitors with a central substituted proline moiety and WO 05/073216 with a central cyclopentyl moiety. Amongst these, the macrocyclic derivatives are attractive by their pronounced activity against HCV and attractive pharmacokinetic profile.

WO 2007/014926 describes macrocyclic cyclopentyl and proline derivatives including the compound of formula (I), with the structure represented hereafter. The compound of formula (I) is a very effective inhibitor of the HCV serine protease and is particularly attractive due to its favorable pharmacokinetical profile. Because of its properties this compound has been selected as a potential candidate for development as an anti-HCV drug. Consequently there is a need for producing larger quantities of this active ingredient based on processes that provide the product in high yield and with a high degree of purity. WO 2008/092955 describes processes and intermediates to prepare the compound of formula (I).

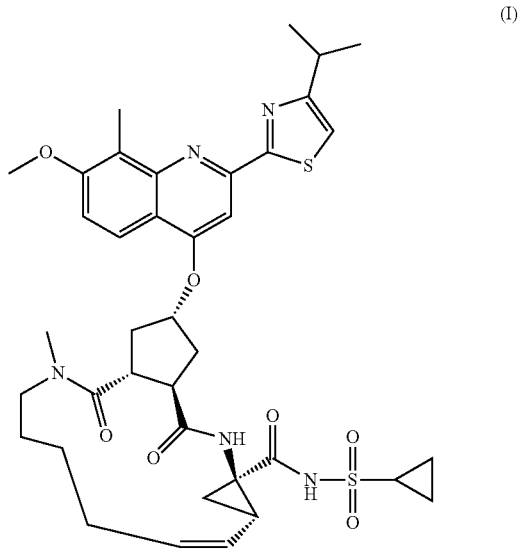 [SMILES: COc1ccc2c(O[C@@H]3C[C@H]4C(=O)N[C@]5(C(=O)NS(=O)(=O)C6CC6)C[C@H]5/C=C\CCCCN(C)C(=O)[C@@H]4C3)cc(-c3nc(C(C)C)cs3)nc2c1C]

(I)

The compound of formula (I) can be prepared starting from an intermediate (VI), wherein the ester function is hydrolysed, yielding carboxylic acid (V), which in turn is coupled in an amide forming reaction with the cyclopropyl amino acid (Va). The resulting intermediate (IV) is cyclized by an olefin metathesis reaction in the presence of a suitable metal catalyst such as e.g. an ylidene Ru-based catalyst. The resulting macrocyclic ester (III) is then hydrolyzed to macrocyclic acid (IV). The latter is coupled with a sulfonylamide (V) in an amide forming reaction to yield the end product (I). These reactions are outlined in the reaction scheme herebelow. In this and the following reaction schemes or representations of individual compounds, R is $C_{1-4}$alkyl, in particular R is $C_{1-3}$alkyl, more in particular R is $C_{1-2}$alkyl, or in one embodiment R is ethyl. $R^1$ is $C_{1-4}$alkyl, in particular $R^1$ is $C_{1-3}$alkyl, more in particular $R^1$ is $C_{1-2}$alkyl, or $R^1$ is methyl; or $R^1$ is ethyl.

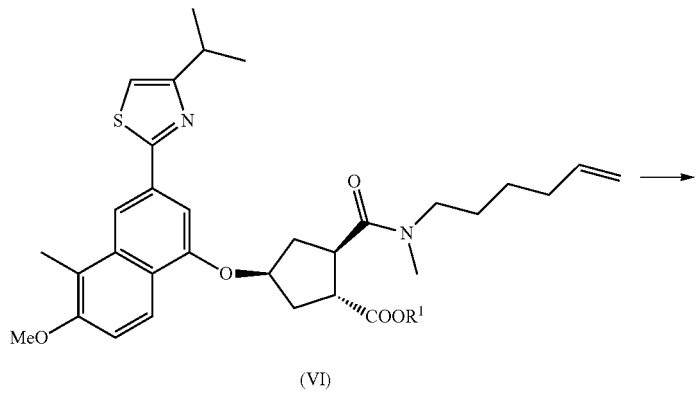

(VI)

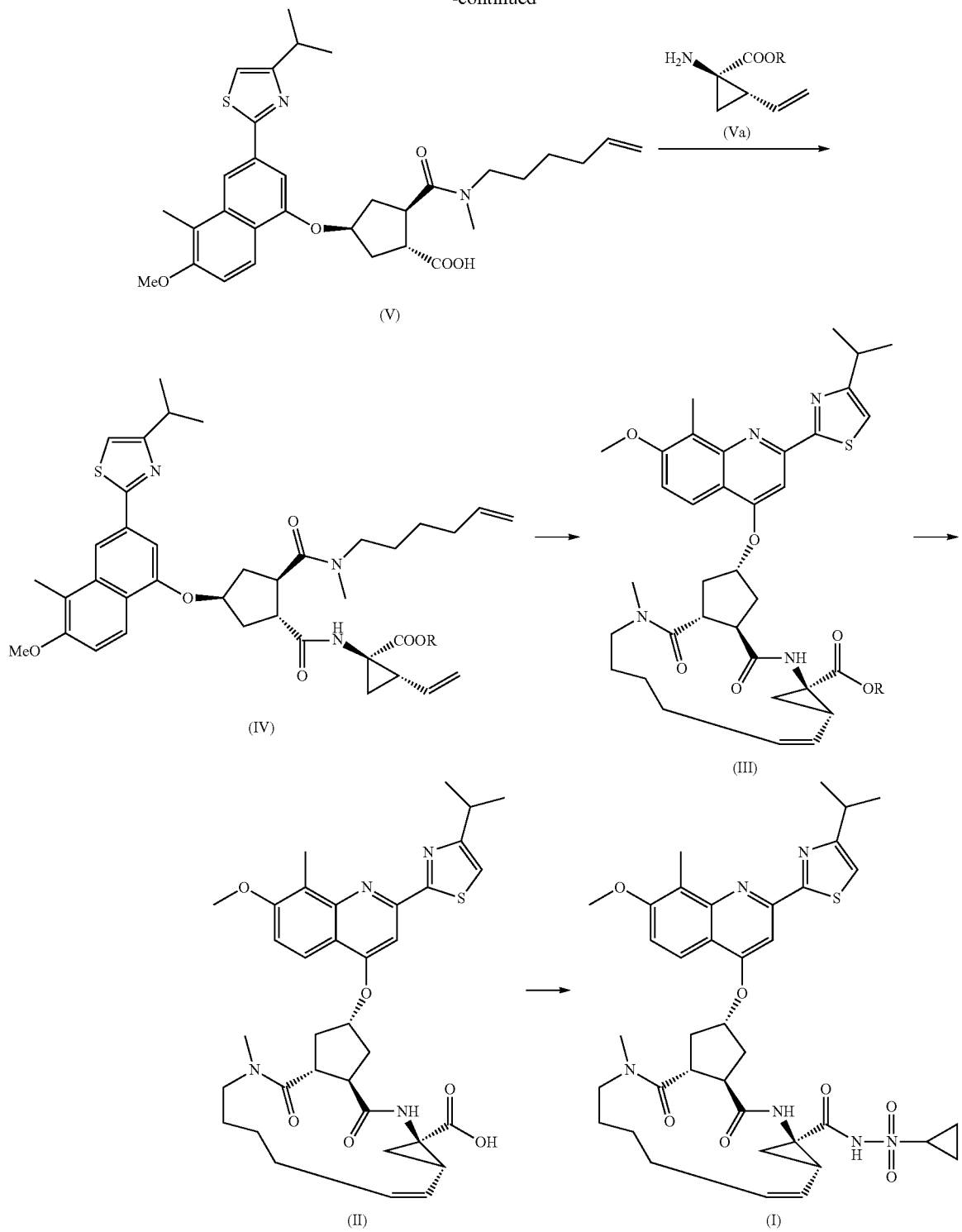

Intermediate (VI) in turn can be prepared using procedures described in WO 2008/092955, in particular starting from a hydroxycyclopentyl bis-ester of formula (Xa), by either (a) reacting the hydroxycyclopentyl bis-ester of formula (Xa) with a thiazolyl substituted quinolinol (VII) in an ether forming reaction, thus obtaining a quinolinyloxycyclopentyl bis-ester of formula (XII), wherein the benzyl ester group that is in cis position vis-à-vis the ether group in the quinolinyloxy-cyclopentyl bis-ester of formula (XII) is selectively cleaved to a mono carboxylic acid (XI), which in turn is coupled with an alkenylamine in an amide forming reaction, thus obtaining the desired end product of formula (VI); or (b) selectively converting the hydroxycyclopentyl bis-ester of formula (Xa) to the mono carboxylic acid (IX), which in turn is coupled with an alkenylamine in an amide forming reaction to obtain hydroxycyclopentylamide (VIII), which in turn is reacted with a thiazolyl substituted quinolinol (VII), thus obtaining the desired end product of formula (VI); as outlined in the following reaction scheme:
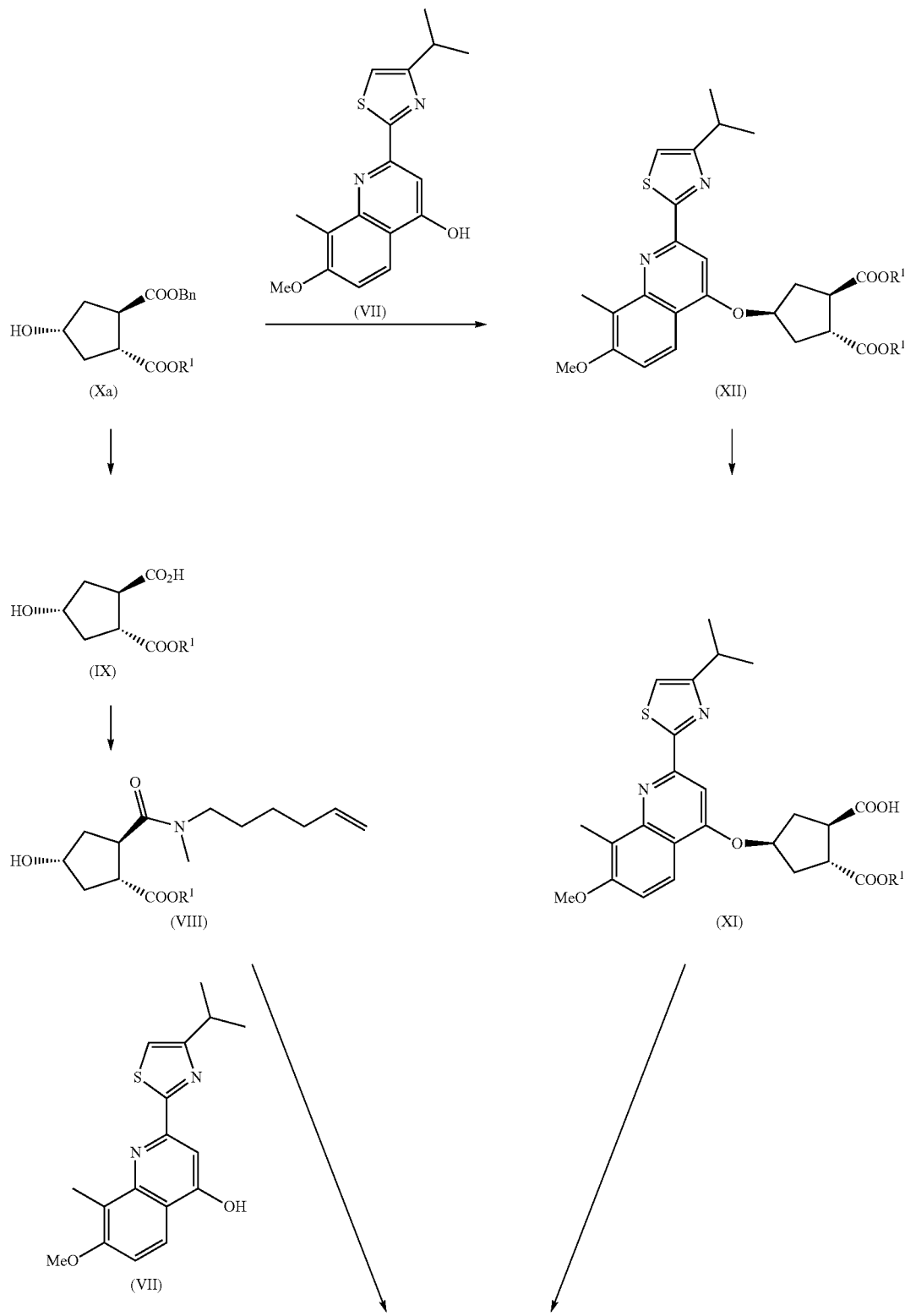

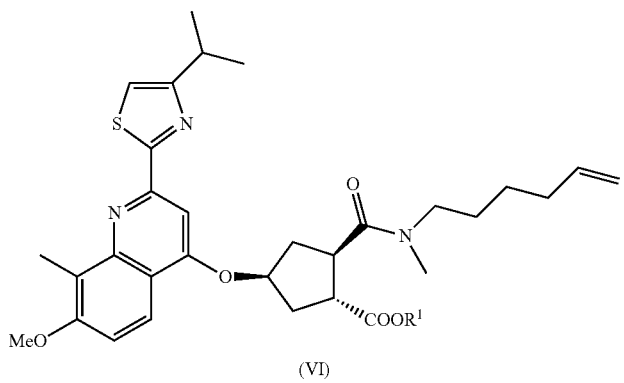

(VI)

Each R[1] in the processes represented in the above scheme is as specified above and preferably R[1] is methyl. Bn represents benzyl.

The presence of various chiral centers in the compound of formula (I) and its predecessors poses particular challenges in that chiral purity is essential to have a product that is acceptable for therapeutic use. The intermediate (VI) has three chiral centers and getting the correct stereochemistry for all three centers is an important challenge for any synthesis processes aimed at preparing this compound. Hence the processes for preparing (VI) should result in products of acceptable chiral purity without use of cumbersome purification procedures with the loss of substantial amounts of undesired stereoisomeric forms.

WO 2008/092955 describes a synthesis procedure for intermediate (Xa) starting from 4-oxo-cyclopentyl-1,2-bis-carboxylic acid (XVII) by reducing the keto function to an alcohol, thus obtaining 4-hydroxy-cyclopentyl-1,2-bis-carboxylic acid (XVI), which in turn is cyclized to the bicyclic lactone (XV), wherein the carboxylic acid group in the bicyclic lactone (XV) is esterified with benzyl alcohol thus obtaining the lactone benzyl ester (XIV). The lactone in the latter is opened by a transesterification reaction in the presence of a $C_{1-4}$alkanol, thus yielding the hydroxycyclopentyl bis-ester of formula (X), which in turn is resolved in enantiomers (Xa) and (Xb); as outlined in the following reaction scheme:

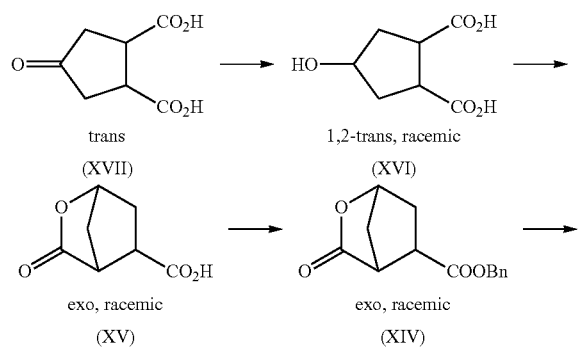

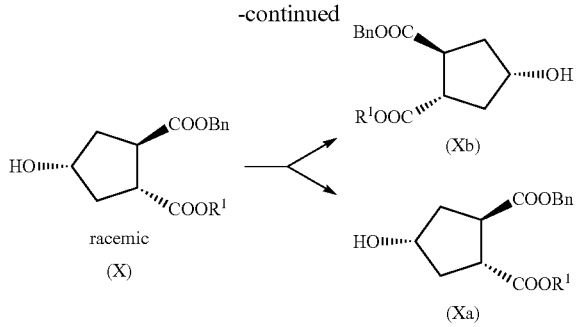

Each R[1] in the processes represented in the above scheme is as specified above and preferably R[1] is methyl.

A disadvantage of the above process is that it involves a resolution of the enantiomers of (X) by chiral column chromatography, a cumbersome procedure that is difficult to run at large scale production.

Honda et al., Tetrahedron Letters, vol. 22, no. 28, pp 2679-2682, 1981, describes the synthesis of (±)-brefeldin A using the following starting materials:

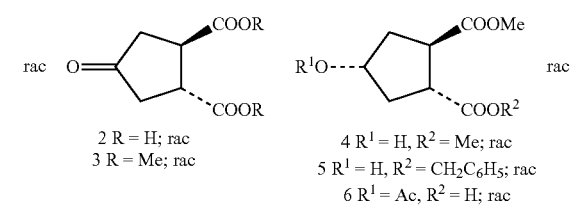

2 R = H; rac
3 R = Me; rac

4 R[1] = H, R[2] = Me; rac
5 R[1] = H, R[2] = CH$_2$C$_6$H$_5$; rac
6 R[1] = Ac, R[2] = H; rac The synthesis of Honda et al. starts from dl-trans-4-oxo-cyclopentane-1,2-dicarboxylic acid 2, which was esterified to the corresponding methyl ester 3, and reduced with Raney-Ni to the alcohol 4. Partial hydrolysis of 4 to the monocarboxylic acid and benzylation with benzyl bromide gave predominantly diastereoisomer 5, namely the diastereoisomer wherein the hydroxy and benzyl ester groups are in cis position. The latter ester 5 in Honda et al. and compound (X) are both racemates, but are diastereoisomers of each other, more precisely epimers on the carbon no. 4 bearing the hydroxy group. Compound (Xa) is one of the two enantiomers obtained by separation from the racemic compound (X). The other enantiomer is compound (Xb).

WO 2005/073195 describes the synthesis of enantiomerically pure bicyclic lactone (8b) starting from an enantiomer of 3,4-bis(methoxycarbonyl)cyclopentanone. The latter was prepared as described by Rosenquist et al. in Acta Chemica Scandinavica 46 (1992) 1127-1129. The trans (3R,4R)-3,4-bis(methoxycarbonyl)cyclopentanone isomer was converted to the bicyclic lactone (8b):

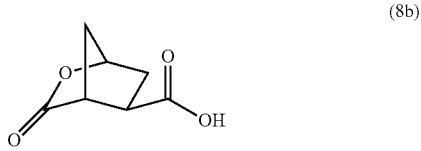 [SMILES: O=C(O)C1CC2CC1C(=O)O2]

(8b)

WO 2005/073195 additionally describes further modification of lactone (8b) to the t.Bu ester, opening of the lactone and coupling with appropriately protected amino acids, e.g. with (1R,2S)-1-amino-2-vinylcyclopropane carboxylic acid ethyl ester, which in the latter instance yields:

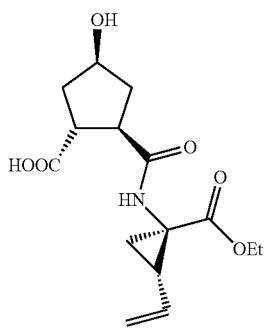

The build-up of the compounds of formula (I) necessarily involves introducing the thiazolyl substituted quinoline moiety on the cyclopentyl ring via an ether linkage. The Mitsunobu reaction offers an attractive reaction route for preparing aromatic alkylethers in which an alkyl ether is activated and reacted with a phenol. In addition, Mitsunobu reactions are in general more efficient than the O-arylation reactions, which require additional synthesis steps. In this mild reaction the stereochemistry of the alkyl part is inverted. The reaction gives rise to side products, such as R'OOC—NH—NH—COOR', wherein R' is $C_{1-4}$alkyl and in particular ethyl or isopropyl, other nitrogen-containing compounds, and triphenylphosphine oxide, which need to be separated from the desired end product.

The processes of the present invention are advantageous in that they are suitable for large scale production. Cumbersome purification steps, in particular by chromatography, are avoided. Essential in the synthesis of the compound of formula (I) is the built-up of the cyclopentyl moiety with the right stereochemistry at its three chiral centers.

One of the aspects of this invention concerns processes for preparing the intermediates (VIII) in high yield and purity, especially in terms of chiral purity, that are fit for large scale industrial application.

The present invention is aimed at providing procedures to prepare cyclopentyl intermediates with the right stereochemistry, in high yield and purity. In particular the present invention concerns the preparation of the intermediates

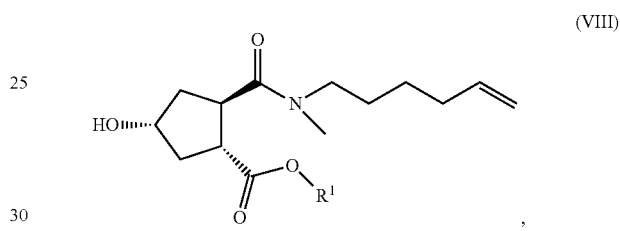

(VIII)

which find use in the procedures to prepare the compound of formula (I).

DESCRIPTION OF THE INVENTION

In one aspect, the present invention relates to a process for preparing a compound of formula (VIII), starting from an cinchonidine salt (XXa), which is reacted with N-methylhexenamine (NMHA) (XIX) in an amide-forming reaction to yield the bicyclic lactone amide (XVIII), in which the lactone group is opened to yield the desired product (VIII). These reactions are illustrated in the scheme below, wherein $R^1$ is as specified above.

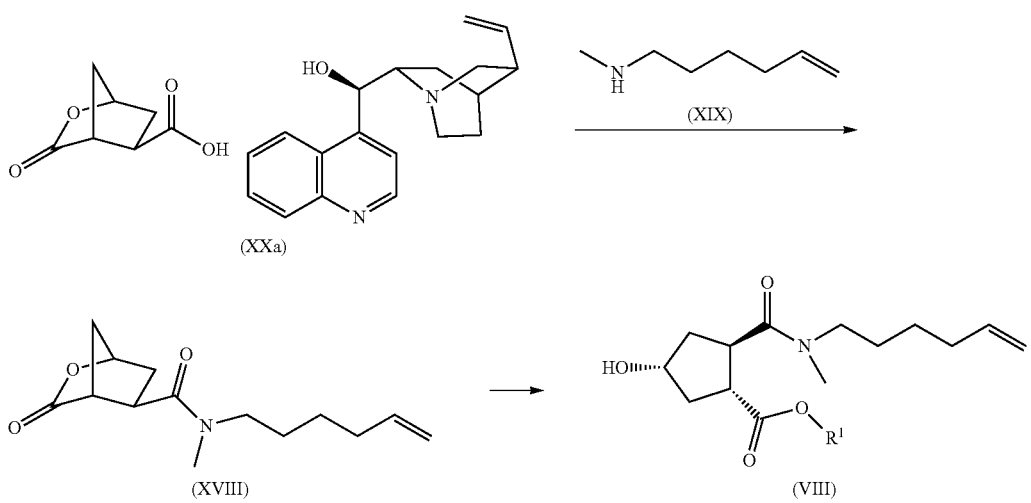

In a further aspect the invention concerns the preparation of the cinchonidine salt (XXa), which is obtained by the resolution of the diastereoisomeric salt mixture (XX) by selective crystallization of (XXa). The salt (XX) in turn is obtained by forming the cinchonidine salt of the racemic bicyclic lactone carboxylic acid (XV), as outlined in the following reaction scheme:

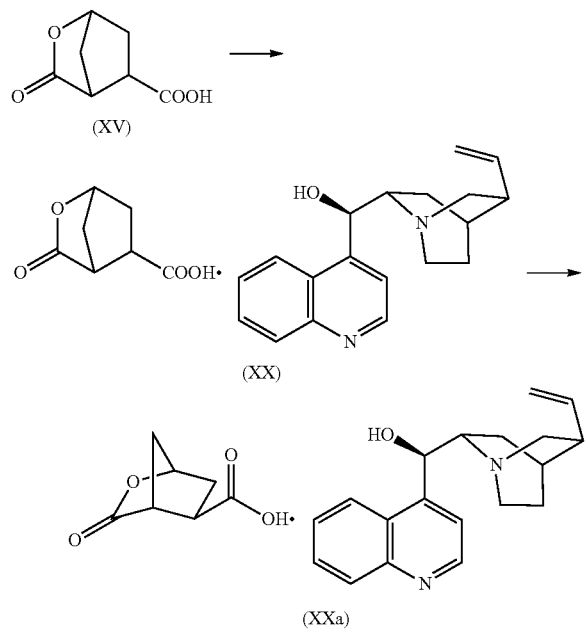

In still a further aspect, the invention concerns the cinchonidine salt of formula

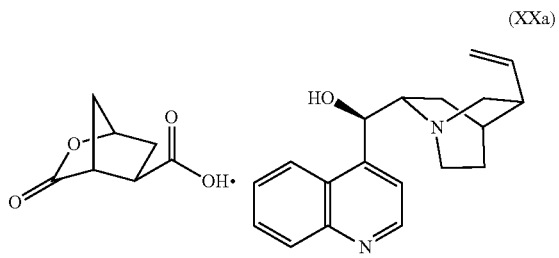

This salt is useful as intermediate in the preparation of intermediate (VIII), and therefore also in the preparation of the HCV inhibitor (I).

The synthesis procedures of the present invention offer the advantage that the correct stereochemistry at the cyclopentyl moiety is obtained and this without using chiral chromatography. The cinchonidine salt (XXa) has been found to selectively crystallize with high chiral purity.

The reaction of the cinchonidine salt (XXa) with NMHA (XIX) is an amide forming reaction, which comprises reacting the starting materials with an amide-coupling reagent in a reaction-inert solvent, optionally in the presence of a base. Solvents that can be used comprise halogenated hydrocarbons such as dichloromethane (DCM) or chloroform, ethers such as tetrahydrofuran (THF) or 2-methyltetrahydrofuran (MeTHF), alcohols such as methanol or ethanol, hydrocarbon solvents such as toluene or xylene, dipolar aprotic solvents such as DMF, DMA, acetonitrile, or mixtures thereof. Preferred are dichloromethane, MeTHF, methanol, ethanol, toluene, or mixtures thereof. Amide-coupling agents comprise agents such as N-ethoxycarbonyl-2-ethoxy-1,2-dihydroquinoline (EEDQ), N-isopropoxycarbonyl-2-isopropoxy-1,2-dihydroquinoline, in particular its hydrochloride salt, (IIDQ), N,N,N',N'-tetramethyl-O-(7-azabenzotriazol-1-yl)uronium hexafluorophosphate (HATU), benzotriazol-1-yl-oxy-tris-pyrrolidino-phosphonium hexafluorophosphate (commercially available as PyBOP®), 1,1'-Carbonyldiimidazole (CDI), 1-ethyl-3-(3-dimethylaminopropyl) carbodiimide (EDI or EDCI) as well as its hydrochloride salt, dicyclohexyl-carbodiimide (DCC), or 1,3-diisopropylcarbodiimide, O-benzotriazole-N,N,N',N'-tetramethyl-uronium-hexafluoro-phosphate (HBTU) and the like. A catalyst may be added, for example 1-hydroxybenzotriazole (HOBt) or 4-dimethylaminopyridine (DMAP). The reaction is usually conducted in the presence of a base, in particular an amine base such as a tertiary amine, e.g. triethylamine, N-methylmorpholine, N,N-diisopropylethylamine, (the latter also being referred to as Hünig's base, DIPEA, or DIEA). Preferably, no base is used. In one embodiment, the reaction is conducted in DCM or MeTHF with EEDQ, optionally with addition of methanol at the end of the reaction, at reflux temperature of the reaction mixture.

In an alternative embodiment, the salt (XXa) can be split into cinchonidine and the bicyclic lactone, and the latter can be reacted with NMHA in an amide forming reaction as described above. It has been found that the cinchonidine salt (XXa) itself can be used in the amide forming reaction and the cinchonidine can afterwards be removed easily in the work-up of the reaction mixture, for example by treatment of the latter with an acid such as HCl, and washing away the side products with aqueous phases.

The lactone functionality in the resulting bicyclic lactone amide (XVIII) is opened by a transesterification reaction with an alcohol, which may also serve as a solvent, in particular a $C_{1-4}$alkanol such as methanol or ethanol, in the presence of an acid. Acids that can be used are strong organic acids such as sulfonic acids, in particular methanesulfonic acid. A solvent can be added such as an ether, in particular THF or MeTHF; or hydrocarbon solvents such as toluene or xylene. The transesterification reaction yields the ester of the alcohol that is used, e.g. when conducting the reaction in methanol, the methyl ester is formed.

The cinchonidine salt (XX) in turn can be prepared by treating the racemic bicyclic lactone carboxylic acid (XV) with cinchonidine. Typically the racemic salt (XX) is not isolated, but kept in solution while the desired isomer (XXa) is allowed to crystallize. In one embodiment, a suspension of cinchonidine is added to a solution of (XV) at slightly elevated temperature and subsequently allowing the mixture to cool whereupon the desired salt (XXa) crystallizes. Further purification may comprise recrystallization. Suitable solvents for dissolving (XV) include ester solvents such as ethyl acetate, whereas suitable solvents for the cinchonidine suspension include acetonitrile. In one embodiment the salt formation is done at a temperature of about 50 to about 70° C., in particular at about 60° C., and the mixture is allowed to cool to about room temperature, such as a temperature in the range from about 20 to about 25° C., e.g. at about 22° C. Further purification can be done by recrystallization from an appropriate solvent or solvent mixture, in particular an alcohol such as a $C_{1-4}$alkanol, e.g. isopropanol, or by re-slurrying in a solvent or solvent mixture, e.g. an ethanol/water mixture such as a 5%/95% (w/w) water/ethanol mixture.

The finding that the salt (XXa) can be isolated by crystallization provides an elegant way to obtain the bicyclic lactone in high enantiomeric purity. Recrystallization or reslurrying allows further purification of this salt. (XXa) can be used as a starting material in the further synthesis of intermediates (XVIII) and (VIII), as described above. The latter in turn can be converted to intermediate (VI), an important building block in the preparation of the compound of formula (I).

The racemic bicyclic lactone carboxylic acid (XV) is prepared as described in WO 2008/092955 and as outlined above in the scheme illustrating the preparation of (Xa) and (Xb). In particular, (XV) is prepared by reducing the ketocyclopentane biscarboxylic acid (XVII) to the corresponding hydroxycyclopentane biscarboxylic acid (XVI), which subsequently is converted to (XV) by lactone formation. The keto to hydroxy reduction in (XVIII) can be done by hydrogen in the presence of a noble metal catalyst, e.g. rhodium on carbon (Rh/C) or Raney Ni, in a reaction-inert solvent, e.g. in water. The resulting hydroxycyclopentane biscarboxylic acid (XVI) can be converted to a salt, e.g. a tertiary amine salt such as the triethylamine salt.

Cyclization via lactone formation of (XVII) can be done by reaction with a chloro-formate, e.g. with ethyl or methyl chloroformate. This reaction is done in a reaction-inert solvent such as a ketone, in particular acetone, or an ether such as THF or MeTHF, or acetonitrile. A base can be added, e.g. a tertiary amine such as triethylamine

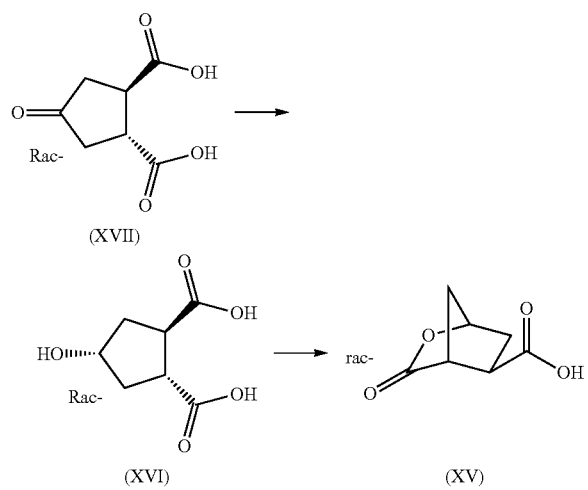

In one embodiment, the present invention relates to the use of the compounds of formula (XX) or (XXa) as intermediates in the preparation of the compound of formula (I), or the salts thereof.

In another embodiment, the present invention relates to the compounds per se of formula (XX) or (XXa). These compounds may be in isolated form, or in solution. In particular, the compounds of formula (XX) or (XXa) are isolated in solid form.

The further processing of the compounds of formula (VIII) to the end products of formula (I) are as outlined in the reaction schemes above and in particular as outlined in WO 2008/092955. This further processing comprises a Mitsunobu reaction, which involves the inversion of the stereochemistry of the cyclopentyl carbon bearing the hydroxy group.

The intermediate of formula (VI) is crystallizable, in particular when mixed with an alcoholic solvent, more in particular when mixed with a $C_{1-4}$alkanol. Crystallization of the intermediate of formula (VI) allows controlling the purity of this compound as well as any compounds derived therefrom in subsequent process steps. In particular this property allows the preparation of the intermediate of formula (VI) in greater enantiomeric purity.

This crystallization of intermediate (VI) not only allows to remove the side products of the Mitsunobu reactions that yield these compounds, but also to subsequently separate intermediate (VI) from its reaction mixtures in a simple way. This separation is easily done by effecting a solvent change, in particular by adding an alcoholic solvent to the reaction mixture obtained from the Mitsunobu reactions, without having to manipulate any further the reaction mixture or any component thereof. Further, since intermediate (VI) is not soluble in an alcoholic solvent, while the by-products are, this offers immediate purification of intermediate (VI) from the reaction mixture.

As used in the foregoing and hereinafter, the following definitions apply unless otherwise noted. The term halo is generic to fluoro, chloro, bromo and iodo. The term "$C_{1-4}$alkyl" defines straight or branched chain saturated hydrocarbon radicals having from 1 to 4 carbon atoms such as for example methyl, ethyl, 1-propyl, 2-propyl, 1-butyl, 2-butyl, 2-methyl-1-propyl, 2-methyl-2-propyl. "$C_{1-3}$alkyl" is generic to methyl, ethyl, 1-propyl, and 2-propyl. "$C_{1-2}$alkyl" is generic to methyl and ethyl. The term $C_{1-4}$alkanol refers to an alcohol derived from a $C_{1-4}$alkyl group.

The generally accepted convention for representing stereochemical compounds, which is also adhered to herein, is the following:

A compound represented without stereobonds, e.g. compound (XV), is racemic or the configuration of the stereogenic center(s) is not defined.

A compound represented with stereobonds and one of the descriptors "(±)", "rel", or "rac", is racemic and the stereochemistry is relative.

A compound represented with stereobonds but without the descriptors "(±)", "rel", or "rac" refers to a non-racemic compound (scalemic substance) or an enantio-enriched, i.e. the stereochemistry is absolute.

For instance, in the Honda et al. reference the designation "(±)" is used in the title of the article, meaning that there is described a racemic synthesis with racemic intermediates. However the above convention may not necessarily be followed in all publications.

The chiral purity is given as enantiomeric ratio (e.r.). For the salts, the e.r. value refers to the ratio of the two enantiomers in the diastereomeric mixture. See for example intermediate (XV).

In certain embodiments, the term "about" when used in relation to a numerical value can be left out so that the exact value is meant. In other embodiments this term can mean the numerical value to which it is linked ±10%, or ±5%, or ±1%.

EXAMPLES

The following examples are intended to illustrate the present invention and should not be construed as a limitation of the scope of the present invention.

Example 1

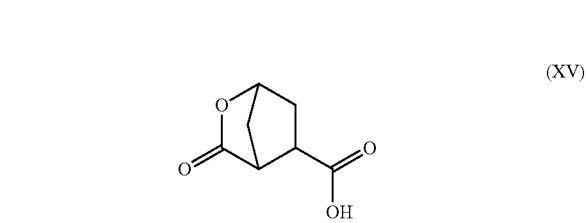 [SMILES: O=C(O)C1CC2CC1C(=O)O2]

To a suspension of 32.7 g (0.19 mol) of intermediate (XVII) (racemic) in 237.5 ml water under an atmosphere of nitrogen was added 1.0 ml (0.019 mol) 50% wt/wt aqueous NaOH. Warm the mixture to 60° C. and add 2.5 g Rh/C (5% wt/wt). The reaction flask was purged with hydrogen and stirred under an atmosphere of hydrogen until complete conversion was reached. The warm reaction mixture was filtered over Celite. The filter cake was washed twice with 10 ml water. Triethylamine (55.61 ml, 0.40 mol) was added and 80% of the solvent volume was distilled off under a pressure of 30 mbar. The reaction flask was fitted with a Dean-Stark trap filled with 2-methyl-tetrahydrofuran. 2-Methyltetrahydrofuran (100 ml) was added to the reaction mixture, which was refluxed for 4 hours to remove the remaining water. 80% of the solvent volume was distilled off under ambient pressure. The mixture was cooled to 50° C. and acetone (380 ml) added. The mixture was cooled further to 22° C. and again acetone (760 ml) was added. The resulting suspension was cooled under an atmosphere of nitrogen to −5° C. and triethylamine (27.8 ml, 20.24 g, 0.2 mol) was added. Then ethyl chloroformate (22.68 g, 0.21 mol) was added dropwise and the mixture was stirred at 0° C. for 3 hours. The reaction mixture was warmed to 22° C. and stirred for a further 12 hours, then filtered over dicalite and the solids were washed with acetone (100 ml). The resulting solution of (XV) in acetone was used in the following example to prepare its cinchonidine salt.

Example 2

Preparation of Cinchonidine Salt (XXa)

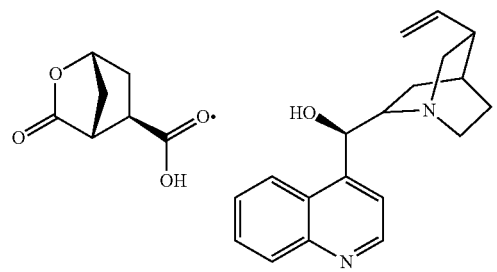

(XXa)

Method 1

Approximately 80% of the solvent volume was distilled off under atmospheric pressure. Ethyl acetate (190 ml) was added and the organic solution was washed with aqueous HCl (2M, 114 ml), yielding a solution of (XV) in ethyl acetate. The solution of (XV) in ethyl acetate was added to a suspension of cinchonidine (55.94 g, 0.19 mol) in acetonitrile (760 ml) at 60° C. The resulting mixture was stirred at 60° C. for 10 minutes and then cooled to 22° C. and filtered. The solids were recrystallized from isopropanol (1500 ml) to yield after drying 24.8 g (29% yield) of a white solid. Chiral purity: e.r.: 89/11

H-NMR (DMSO-d6-400 MHz), δ ppm 1.45-1.86 (m, 6 H), 1.93-2.19 (m, 3H), 2.32 (br s, 1H), 2.56-2.80 (m, 2H), 2.90-3.07 (m, 2 H), 3.12-3.29 (m, 1H), 3.30-3.52 (m, 1H), 4.93-5.03 (m, 3H), 5.52 (d, J=5.6 Hz, 1H), 5.80-5.89 (m, 1H), 7.5 (d, J=4.2 Hz, 1H), 7.6 (t, J=5.6 Hz, 1H), 8.0 (d, J=9.3Hz, 1H), 8.3 (d, J=8.1Hz, 1H), 8.8 (d, J=4.6Hz, 1H), Method 2

Approximately 80% of the solvent volume was distilled off under atmospheric pressure. Ethyl acetate (522 ml) was added and approximately 50% of the solvent volume was distilled off. The remainder was cooled to 22° C. and ethyl acetate (180 ml) was added. The resulting suspension was filtered and the filtrate added to a suspension of cinchonidine (55.94 g, 0.19 mol) in acetonitrile (760 ml). This mixture was warmed to 60° C., stirred for 10 minutes, then cooled to 22° C. and filtered. The solids were recrystallized from isopropanol (1500 ml) to yield after drying 24.8 g (29% yield) of a white solid. Chiral purity: e.r.: 90/10

Method 3

Following the procedure of Method 2, but changing the suspension of cinchonidine (55.94 g, 0.19 mol) in acetonitrile (760 ml) by a suspension of cinchonidine (55.94 g, 0.19 mol) in isopropanol (325 ml) and ethanol (325 ml), there were obtained 24.8 g (29%) of a white solid. Chiral purity: e.r.: 92/8.

The chemical purity of (XXa) as well as the e.r. can be increased by either recrystallisation or re-slurry of the salts, as described in the following three procedures.

12 g of crude (XXa) (chemical purity: acid titration: 96.2%, base titration 102.2%; chiral purity: e.r.: 78.7/21.3) was dissolved in 500 ml refluxing 2-propanol. The mixture was allowed to cool slowly. If the crystallisation did not begin spontaneously, the mixture was seeded with (XXa) at 40° C., then stirred at this temperature for 2 hours. After cooling to room temperature, the mixture was stirred further for 2 hours, filtered and washed with 50 ml of 2-propanol to give, after drying in vacuum at 50° C., 5.51 g of white product. Chemical purity: acid titration 99.6%, base titration 98.4%; chiral purity: e.r.: 88.1/11.9.

A mixture of 5.3 g (XXa) with e.r. 87.0/13.0 and 0.5 g (XXa) with e.r.: 90.6/9.4 was dissolved in 160 ml refluxing ethanol containing 5 wt % of water. The clear solution was allowed to cool slowly. If the crystallization did not begin spontaneously, the mixture was seeded with (XXa) at 45° C. After cooling to room temperature, the mixture was stirred further for 14 hours, filtered and washed with 10 ml of ethanol containing 5 wt % of water to give, after drying in vacuum at 50° C., 4.21 g of white product. Chiral purity: e.r.: 96.5/3.5

A mixture of 25 g (XXa) with e.r. 87.0/13.0 and 2.5 g (XXa) with e.r.: 90.6/9.4 was heated to reflux in 160 ml ethanol containing 5 wt % of water. After 1 hour at reflux, the slurry was allowed to cool to room temperature over 2 hours and stirred further for 14 hours. The mixture was then filtered and washed with 15 ml of ethanol containing 5 wt % of water to give, after drying in vacuum at 50° C., 22.96 g of white product. Chiral purity: e.r.: 97.6/2.4

Example 3

Preparation of (XVI) and its Triethylamine Salts (XVIa)

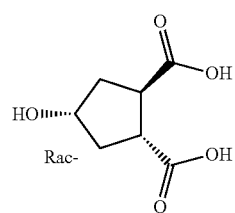

(XVI)

(a) 344 mg (2 mmol) (XVII) and 725 mg (4 mmol) tetramethylammonium hydroxide pentahydrate were dissolved in a mixture of 2.5 ml methanol and 2.5 ml MeTHF. The solution was stirred overnight at room temperature under hydrogen atmosphere in the presence of 82 mg wet 5% rhodium on charcoal as a catalyst. The catalyst was filtered off and the filtrate was diluted to a final volume of 100 ml with methanol. LC analysis showed that 46.% (XVI) was formed as its bis (tetramethylammonium) salt while 41% (XVII) was still present as its bis(tetramethylammonium) salt.

(b) To 400 g of a 6.6 wt/wt % (XVI) solution in water was added 44.4 ml triethylamine 330 g solvent was distilled off under vacuum, then the oily residue was allowed to cool to 50° C. and 51.5 ml acetone was added thus obtaining a suspension. This suspension was cooled to room temperature and 155 ml more acetone was added. The suspension was cooled to 5° C. and stirred overnight at that temperature. The solid was filtered, washed with cold acetone and dried at 70° C. under vacuum thus obtaining 15.05 g (XVI) as its complex with various amounts of triethylamine (XVIa) as a white crystalline powder. Yield: 37%. For example (XVI) as its complex with ⅓, or with 2 triethylamine could be obtained.

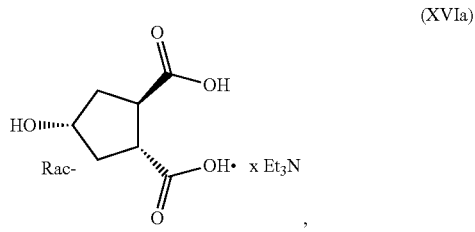

(XVIa)

wherein x is between ⅓ and 3, e.g. x is ⅓; x is 2.

Purification of (XVIa)

(a) 2.00 g crude (XVIa) was suspended in 10.4 ml acetone and the suspension was brought to reflux before being allowed to cool down to room temperature. The solid was filtered, washed with acetone and dried at 50° C. under vacuum to give 210 mg pure (XVIa) as a white powder. Yield: 35%.

(b) 2.00 g crude (XVIa) was suspended in 10.4 ml butanol and the suspension was brought to reflux before being allowed to cool down to room temperature. The solid was filtered, washed with acetone and dried at 50° C. under vacuum to give 190 mg purified (XVIa) as a white powder. Yield: 14%.

Example 4

Preparation of (XVIII)

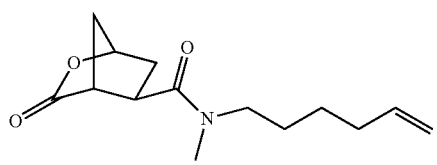 [SMILES: C=CCCCCN(C)C(=O)C1CC2CC1C(=O)O2]

(XVIII)

(a) 14.18 g (31.5 mmol) (XXa) (e.r.: 90/10), 3.92 g (34.6 mmol) NMHA and 8.56 g (34.6 mmol) EEDQ were suspended in 157 ml DCM and the resulting suspension was refluxed overnight. 47.2 ml methanol was added and the reflux was prolonged overnight. The reaction mixture was then concentrated under vacuum and the residue was partitioned between 47 ml toluene and 79 ml aqueous 1M HCl. The organic layer was successively washed with 31.5 ml water, 31.5 ml aqueous 1M NaOH and 31.5 ml water, then concentrated under vacuum to give 11.93 g crude (XVIII) (e.r. 90/10), which was used without purification in the next step.

(b) 2.50 g (5.55 mmol) (XXa), 691 mg (6.10 mmol) NMHA and 1.51 g (6.10 mmol) EEDQ were suspended in 28 ml THF and the suspension was refluxed for 2 days. 22 ml toluene was added and 28 ml solvent was distilled off. After cooling to 50-60° C., 19.4 ml aqueous 1N HCl was added and the two layers were separated. The organic layer was washed with 5.6 ml water then concentrated under vacuum and the residue was purified by flash chromatography to give 910 mg (XVIII). Yield: 65%.

$^1$H NMR (CDCl$_3$, 600 MHz, two rotamers present, ratio 55/45): ppm 1.26-1.38 (m, 2 H), 1.43-1.60 (m, 2 H), 2.01 (m, 2 H), 2.07-2.21 (m, 4 H), 2.86 (s, 3 H—minor rotamer), 2.89-2.97 (m, 2 H), 2.97 (s, 3 H—major rotamer), 3.21 (ddd, 1 H—minor rotamer, J=14.7, 9.1, 5.8 Hz), 3.29 (m, 1 H—minor rotamer), 3.31 (t, 2 H, J=7.6 Hz–major rotamer) 4.87-4.93 (m, 2 H) 4.96 (d, 1 H, J=16.2 Hz) 5.71 (m, 1 H).

$^{13}$C NMR (CDCl$_3$, 150 MHz, two rotamers present): major rotamer: ppm 25.86, 26.39, 33.24, 33.94, 35.17, 37.43, 37.97, 45.71, 47.95, 80.67, 114.71, 138.26, 170.91, 177.33—minor rotamer: ppm 25.7, 27.72, 33.14, 33.69, 34.29, 36.72, 38.02, 46.19, 49.61, 80.64, 115.22, 137.73, 171.17, 177.28.

(c) 17.85 g (39.6 mmol) (XXa) (e.r.: 97.6/2.4), 4.71 g (41.6 mmol) and 10.78 g (43.6 mmol) EEDQ were suspended in 198 ml MeTHF. The suspension was refluxed 2 days then cooled to room temperature. The solid materials (consisting mostly of cinchonidine) was filtered off and rinsed with toluene. To the combined filtrate were added 40 ml water and 7.14 ml concentrated HCl. The resulting two layers were separated and the organic one was washed with 20 ml water, dried over magnesium sulfate, filtered and concentrated under vacuum. The residue was purified by chromatography through silica gel (eluent: ethyl acetate-heptane: 65/35) to give 9.35 g (XVIII) as an oil. Yield: 68%.

Example 5

Preparation of (VIIIa), which is the Intermediate of Formula (VIII) wherein R$^1$ is Methyl

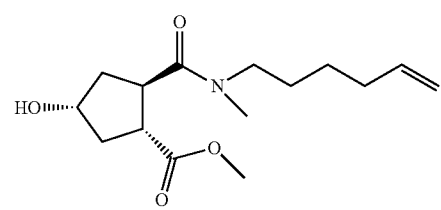

(VIIIa)

(a) 1.05 g (4.2 mmol) (XVIII) was dissolved in 25 mL methanol. 0.014 mL (0.2 mmol) methanesulfonic acid was added and the reaction mixture was stirred three days at room temperature. The volatiles were removed under vacuum and the residue was redissolved in toluene-aqueous 0.33 M NaOH mixture 15 mL each). The layers were separated and the organic layer was dried over magnesium sulfate and concentrated under vacuum to give 330 mg crude (VIIIa) as an oil (yield: 28%).

(b) 20.0 g (44.4 mmol) (XXa), 5.53 g (48.8 mmol) NMHA and 12.08 g (48.8 mmol) EEDQ were suspended in 222 ml methanol. The mixture was refluxed for 24 hours then 178 ml toluene was added. 250 ml solvents were distilled off and the resulting suspension was cooled to 30° C. 155 ml aqueous 1M HCl was added and the two layers were separated. The water layer was extracted twice with 44 ml toluene. The combined organic layers were dried over magnesium sulfate and filtered giving 122.78 g of 4.1 wt/wt % (VIIIa) solution in toluene. Yield: 40%.

(c) 18.42 g of 4.1 wt/wt % (VIIIa) solution in toluene was concentrated under vacuum and the residue was purified by flash chromatography (eluent: ethyl acetate-DCM: 15/85) to give 680 mg chemically pure (VIIIa).

(d) 44.06 g (97.8 mmol) (XXa) (e.r.: 92.4/7.6), 12.18 g (107.6 mmol) NMHA and 26.60 g (107.6 mmol) EEDQ were suspended in 490 ml methanol. The mixture was refluxed overnight, then 391 ml toluene was added and 750 ml of the solvents were distilled off 156 ml water and 30.8 ml concentrated HCl were added to the residue. The resulting two layers were separated and the water layer was extracted with 98 ml toluene, then with 98 ml MeTHF. The combined organic layers were dried over magnesium sulfate and filtered to give 384 g 3.6 wt/wt % (VIIIa) solution in MeTHF-toluene. Yield: 50%.

(e) 19 g (42.2 mmol) (XXa) (e.r.: 93.4/6.6), 5.01 g (44.3 mmol) NMHA and 11.46 g (46.4 mmol) EEDQ were suspended in 210 ml THF. The suspension was refluxed overnight, then cooled to room temperature. The solid materials (mostly cinchonidine) were filtered off and rinsed with 84 ml toluene. To the combined filtrates were added 42 ml water and 7.6 ml concentrated HCl. The two layers were separated and the organic layer was washed with 21 ml water, dried over magnesium sulfate, filtered and concentrated under vacuum. The residue was dissolved in 84 ml methanol, 0.14 ml methanesulfonic acid was added and the solution was stirred overnight at room temperature, then refluxed for 24 h before being cooled to room temperature. 223 mg sodium carbonate was added and the mixture was stirred for 1 hour at room temperature. 295 ml toluene was added and 160 ml solvents were distilled off to give 184.9 g of 5.3 wt/wt % (VIIIa) solution in toluene. Yield: 82%.

(f) 19 g (42.2 mmol) (XXa) (e.r.: 93.4/6.6), 5.34 g (47.2 mmol) NMHA and 12.51 g (50.5 mmol) EEDQ were suspended in 210 ml toluene. The suspension was refluxed for 2 days, then cooled to room temperature. A quantitative analysis showed an in situ yield of 80% of (XVIII). The solid materials (mostly cinchonidine) were filtered off and rinsed with 42 ml toluene. To the combined filtrates were added 42 ml water and 7.6 ml concentrated HCl. The two layers were separated and the organic layer was washed with 21 ml water then with 21 ml brine and concentrated by distilling off 206 ml solvents. To the concentrate were added 84 ml methanol and 0.14 ml methanesulfonic acid. The resulting solution was stirred overnight at room temperature. 223 mg sodium carbonate was added and stirring was continued for an additional 1-2 hours. 295 ml toluene was added and the resulting solid materials were filtered off 183 ml of solvents were distilled off to give 180.5 g of 2.7 wt/wt % (VIIIa) solution in toluene. Overall yield of (VIIIa): 41%.

Example 6

Preparation of (VIa), which is the Intermediate of Formula (VI) wherein R¹ is Methyl (VIa)

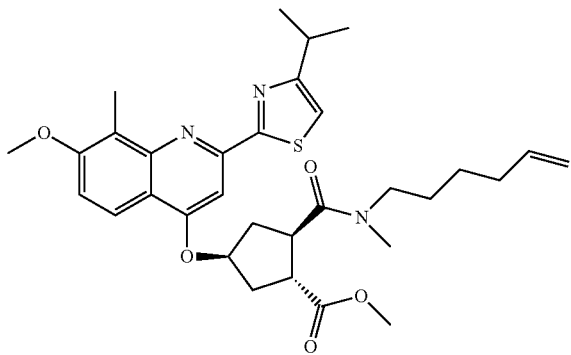

(a) 20.0 g (44.4 mmol) (XXa) (e.r.: 90.1/9.9), 5.53 g (48.8 mmol) NMHA and 12.08 g (48.8 mmol) EEDQ were suspended in 222 ml methanol. The mixture was refluxed for 24 hours, then 178 ml toluene was added. 250 ml solvents were distilled off and the resulting suspension was cooled to 30° C. 155 ml aqueous 1M HCl was added and the two layers were separated. The water layer was extracted twice with 44 ml toluene. The combined organic layers were dried over magnesium sulfate and filtered giving 122.78 g of 4.1 wt/wt % (VIIIa) solution in toluene. To 98.22 g of this solution were added 11.17 g (35.5 mmol) (VII) and 9.78 g (37.3 mmol) triphenylphosphine and the mixture was cooled to 0° C. 7.4 ml (37.3 ml) DIAD was added dropwise, then the resulting reaction mixture was stirred at 0° C. for 2 hours during which a precipitate appeared. 0.1 ml acetic acid was added and the precipitate was filtered off. The filtrate was concentrated under vacuum and the residue was dissolved in 71 ml boiling isopropanol. The solution was cooled to 0° C. allowing (VIa) to crystallize. The solid was filtered, washed with cold isopropanol and dried under vacuum to give 6.32 g (VIa) (e.r.: 97.2/2.8). Yield from (XXa): 31%.

(b) To 382.8 g of 3.6 wt/wt % (48.6 mmol) (VIIIa) solution in MeTHF-toluene, were added 18.53 g (48.6 mmol) (VII) and 19.7 g (75.4 mmol) triphenylphosphine. 118 g of the solvents were distilled off and the resulting residue was cooled to 0° C. 14.9 ml (75.4 mmol) DIAD was added dropwise and the reaction mixture was stirred 2 hours at 0° C. The resulting solid precipitate (mostly triphenylphosphine oxide) was filtered off and washed with cold toluene. 140 g solvents were distilled off from the combined filtrates, then 97 ml 1-butanol was added and 77 g solvents were distilled off. The mixture was cooled to 80° C. and 97 ml isopropanol and 2.43 g dicalite were added. After stirring a few minutes at reflux, the mixture was filtered while hot and the resulting filtrate was cooled to 40° C. 14 mg (VIa) was added as seeding material and the mixture was cooled to 0° C. After stirring overnight at 0° C., 48 ml isopropanol was added and stirring was continued at 0° C. for 2 hours. (VIa) was isolated by filtration, washed with 9.7 ml cold isopropanol and dried at 70° C. under vacuum. A first portion of 8.77 g (VIa) was obtained (yield: 28%). The mother-liquors were concentrated under vacuum and the residue was purified by flash chromatography through silicagel to yield a second crop of (VIa) (12.1 g—yield: 43%).

(c) To 58.9 g (8.3 mmol) of 4 wt/wt % (VIIIa) solution in toluene, were added 2.86 g (9 mmol) (VII) and 2.29 g (10.2 mmol) triphenylphosphine. The suspension was dried by distilling off 27 ml solvent, then cooled to 0° C. 8.7 ml (10.2 mmol) DIAD was added dropwise and the reaction mixture was stirred 1-2 hour at 0° C. The solid materials were filtered off and rinsed with 4.2 ml toluene. From the combined filtrates, 27 ml solvent were distilled off 25 ml 1-butanol was added and 25 ml solvents were distilled off. The residue was cooled to 80° C., 25 ml isopropanol and 415 mg dicalite were added, the suspension was refluxed and filtered while hot. The filtrate was cooled to 30° C. and 2.4 mg (VIa) was added as seeding material. The suspension was cooled to 0° C. and stirred at this temperature overnight. (VIa) was filtered, washed with 2.5 ml cold isopropanol and dried under vacuum, thus obtaining 24.3 g white powder. Yield: 80%.

| Structure | Formula no. |
|---|---|
| Rac- (cyclopentanone with two COOH groups) | (XVII) |
| Rac- (4-hydroxy cyclopentane-1,2-dicarboxylic acid) | (XVI) |
| Rac- (4-hydroxy cyclopentane-1,2-dicarboxylic acid) · x Et₃N; x = 1/3 to 3 | (XVIa) |
| (XV) bicyclic lactone carboxylic acid | (XV) |
| (XV) · cinchonidine | (XX) |
| bicyclic lactone carboxylic acid · cinchonidine | (XXa) |
| bicyclic lactone N-methyl-N-(hex-5-en-1-yl)amide | (XVIII) |

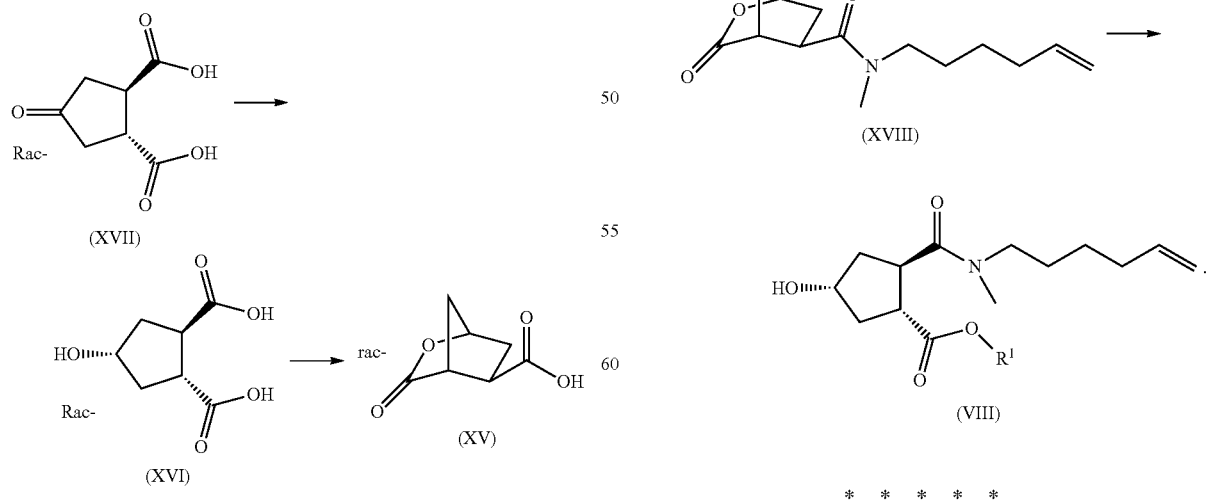

The invention claimed is:

1. A process for preparing the compound of formula VIII, starting from the compound of formula XVII, comprising reducing the by reducing the ketocyclopentane biscarboxylic acid (XVII) to the corresponding hydroxycyclopentane bis-carboxylic acid (XVI), which subsequently is converted to (XV) by lactone formation and reacting the compound (XXA) with N-methyl-hexenamine (NMHA) (XIX) in an amide-forming reaction to yield the bicyclic lactone amide (XVIII), in which the lactone group is opened to yield the desired product (VIII), as illustrated in the scheme below, wherein $R^1$ is $C_{1-4}$alkyl